United States Patent [19]

Tagai et al.

[11] Patent Number: 4,735,857

[45] Date of Patent: Apr. 5, 1988

[54] FIBER GLASS MAINLY COMPOSED OF CALCIUM PHOSPHATE

[75] Inventors: Hideo Tagai, Tokyo; Masahiro Kobayashi, Funabashi; Shigeo Niwa, Aichi; Hiroyasu Takeuchi, Yokoze; Mikiya Ono, Hanno, all of Japan

[73] Assignee: Mitsubishi Mining & Cement Co., Ltd., Tokyo, Japan

[21] Appl. No.: 883,235

[22] Filed: Jul. 8, 1986

Related U.S. Application Data

[62] Division of Ser. No. 624,658, Jun. 26, 1984, Pat. No. 4,613,577.

[30] Foreign Application Priority Data

Jul. 6, 1983 [JP] Japan ................... 58-121646

[51] Int. Cl.$^4$ .................... B32B 9/00; C03C 13/00
[52] U.S. Cl. .................... 428/388; 428/359; 428/361; 428/375; 428/378; 428/389; 501/35; 501/45

[58] Field of Search ............... 428/359, 361, 375, 378, 428/388, 389; 501/35, 45

[56] References Cited

U.S. PATENT DOCUMENTS 4,376,168  3/1983  Takami et al. ................... 501/45

FOREIGN PATENT DOCUMENTS 2087375  5/1982  United Kingdom ................... 501/45

*Primary Examiner*—George F. Lesmes
*Assistant Examiner*—S. A. Gibson
*Attorney, Agent, or Firm*—Jordan and Hamburg

[57] ABSTRACT

A fiber glass is provided for filling in a defect or hollow portion of bone. The fiber glass comprises calcium phosphate as a main ingredient and has a negative zeta potential. The calcium phosphate has a molar ratio of Ca/P of not less than 0.2 and less than 0.6 and the total content of CaO plus $P_2O_5$ less than 80 wt %. The fiber glass is of long filament form or staple fiber form. The fiber glass of long filament form may be woven to form a woven filler.

16 Claims, No Drawings

FIBER GLASS MAINLY COMPOSED OF CALCIUM PHOSPHATE

This is a division, of application Ser. No. 624,658, filed June 26, 1984, now U.S. Pat. No. 4,613,577.

BACKGROUND OF THE INVENTION

1. Field of the Invention

The present invention relates to a fiber glass mainly composed of calcium phosphate, and particularly to a fiber glass for filling in a defect or hollow portion of bone and including calcium phosphate as a main ingredient.

2. Prior Art

In the surgical and orthopedic treatments, prosthesis operations are often required for filling in defects or hollow portions of bone resulting from fracture of bone or surgical removal of bone tumor. Also in the field of dental surgery, similar denture operations are often required for filling in spoilt void portions in maxilla or mandibula resulting from pyorrhea alveolaris. It has been a common practice to resect ilium from the patient to fill up the defect or hollow portion of bone thereby to promote early remedy of the bone tissue. However, by means of such an operaton, normal bone tissue must be picked up from an unspoilt portion which causes additional pain to the patient, and, in addition the operation is very troublesome. Moreover, when the volume of defect or void in the patient's bone is large, the amount of bone obtainable from his own body is not always sufficient for fully filling in the defect or void. In such a case, it is inevitable to use a substitute for the patient's own bone tissue. Although the same or different sorts of bone tissue have been used as the substitute, there remains the problem that the implanted substitute is rejected by the living tissue due to foreign body rejection reaction. For these reasons, the post-operation recovery of the defect is not always satisfactory. Accordingly, such an operation has not yet been recognized as fully satisfactory in practice.

There is, therefore, a demand for an artificial material which is excellent in compatibility with living tissues when filled in a defect or hollow portion of bone to facilitate formation of bone within and at the vicinity of the defect and to promote repair and recovery of the structure and function of the once damaged bone tissue.

A variety of metal alloys and organic materials have hitherto been used as the substitute for the hard tissues in the living body. However, it has been recognized that these materials have the tend to dissolve or otherwise deteriorate in the environment of living tissue or to be toxic to the living body, and that they cause a so-called foreign body reaction. Ceramic materials are used up to date, since they are excellent in compatibility with living body and are free of the aforementioned difficulties. From ceramic materials, particularly alumina, carbon or tricalcium phosphate or a sintered mass or single crystal of hydroxyapatite, which are superior in compatibility with living body artifical bones and teeth have been developed and have attracted a good deal of public attention.

However, the conventional ceramic implant materials have a common disadvantage in that they are inherently too hard and brittle. Therefore, these known ceramic materials are not fully satisfactory in practical use. It has also been attempted to fill in a defect of bone with a sintered ceramic block or a ceramic block of single crystal form. However, since uneven gaps or interstices are formed between the block and the bone tissue, the object of fully filling in the void in the bone cannot be attained. On the other hand, when alumina is used as the filler, it acts as a stimulant to cause absorption of bone at the vicinity of the implanted filler, since alumina is much harder than the bone tissue. The use of ceramic materials has not yet been in the stage of practical application, accordingly. Furthermore, it has not been clarified what properties the ceramic material should have to suppress the foreign body reaction, to improve the compatibility with living body and to promote formation of new bone.

OBJECTS AND SUMMARY OF THE INVENTION

It is, therefore, an object of this invention to provide a fiber glass for filling in a defect or hollow portion of bone, the fiber glass including calcium phosphate as a main ingredient and being excellent in compatibility with living body without causing foreign body reaction, therefore promoting early formation of new bone and unifying integrally with the growing hard tissue of living body.

Another object of this invention is to provide a fiber glass for filling in a defect or hollow portion of bone, the fiber glass including calcium phosphate as a main ingredient and promoting bone formation reaction in the area filled with the fiber glass to realize early remedy and recovery of the structure and function of the once damaged bone tissue.

A further object of this invention is to provide a fiber glass and a cloth or gauze made of the fiber glass for filling in a defect or hollow portion of bone, the fiber glass including calcium phosphate as a main ingredient and being easily formed to have a shape adapted to be closely fitted in the void portion and also adapted to follow the contour of the surrounding living tissues.

A still further object of this invention is to provide a fiber glass for filling in a defect or hollow portion of bone, the fiber glass including calcium phosphate as a main ingredient and being easily formed to have a shape adapted to be fitted in a void of complicated shape.

The above and other objects of this invention will become apparent from the following detailed description of the invention.

A fiber glass for filling in a defect or hollow portion of bone, according to this invention, comprises calcium phosphate as a main ingredient, the fiber glass having a negative zeta potential, the calcium phosphate having a molar ratio of Ca to P of not less than 0.2 and less than 0.6, and the total content of CaO plus $P_2O_5$ being not less than 80% by weight.

DESCRIPTION OF THE INVENTION

The present invention will now be described in detail.

In the first place, the "zeta potential" as used throughout the specification and claims is determined by the streaming potential determination method. In detail, the sample to be determined is pulverized finely and a test cell is filled therewith to form a diaphragm through which a liquid is forcibly passed using an inert gas, such as nitrogen gas, as the pressure source to detect the potential difference between the end faces of the diaphragm-shaped sample. The zeta potential is calculated by substituting the applied pressure and the detected potential difference for P and E in the following equation (Helmholtz-Smoluchowski's equation):

$$\text{Zeta Potential} = (4\pi\eta\lambda E/\epsilon P);$$

wherein $\eta$ is the coefficient of viscosity (poise) of the liquid, $\lambda$ is the specific conductivity ($\Omega^{-1}\text{cm}^{-1}$) of the liquid, $\epsilon$ is the dielectric constant (—) of the liquid in air, E is the detected potential difference (mV) and P is the applied gas pressure (cm $H_2O$).

The glass mainly composed of calcium phosphate used in the present invention is a glass having a negative zeta potential and a molar ratio of Ca of P of not less than 0.2 and less than 0.6 and containing 80%, of weight, or more of the total content of CaO plus $P_2O_5$.

Starting materials for the preparation of the fiber glass mainly composed of calcium phosphate and used in the present invention include a mixture of one or more calcium phosphate compounds with one or more other phosphorous-containing compounds, the calcium phosphate compound being selected from the group consisting of tetracalcium phosphate, hydroxyapatite, tricalcium phosphate and animal bones, the phosphorous-containing compound being selected from the group consisting of triammonium phosphate, ammonium hydrogenphosphate, sodium phosphate and phosphoric acid. A mixture of one or more calcium-containing compounds, such as quick lime, slaked lime and calcium carbonate, mixed with one or more of the phosphorous-containing compounds may also be used. One or more inorganic oxides may be added to the mixture of the calcium phosphate compound with the phosphorous-containing compound or the mixture of calcium-containing compound with the phosphorous-containing compound, if necessary, examples of such inorganic oxides being alumina, silica, sodium oxide, iron oxide, magnesium oxide and kaolin. As has been referred to above, natural animal bones and kaolin may be used in the starting material mixture, provided that a component poisonous to the living body, such as arsenic or cadmium, is not contained therein or the content of poisonous component is negligibly small.

The fiber glass mainly composed of calcium phosphate, according to the present invention, may be prepared by the steps of mixing the aforementioned starting materials to form a material mixture, putting the material mixture into a pot provided with a nozzle at the bottom thereof, melting the mixture to allow the molten mixture to discharge through the nozzle, and blowing a high pressure gas onto the discharged flow of molten mixture, whereby staple fibers are formed. Alternatively, fibers of long filament form may be formed by continuously taking up the spun filaments discharged through the nozzle around a drum or roller.

Since the fiber glass of the invention is extremely flexible to follow the contour of the void which is filled therewith, it is easy to fill in fully the defect or hollow portion of bone with the fiber glass. Formation of new bone is also promoted when a defect or hollow portion of bone is filled with the fiber glass of the invention having a specific surface area larger than that of a glass of lump or bead shape. A further advantage of the use of the filler of fiber or filament form is that continuous void pores are formed within the filler so that new bones extend into the void pores internally of the filler to thus facilitate formation of an integral unified structure in which the filler and the hard tissue of living body adjoin each other.

The fiber glass mainly composed of calcium phosphate, according to the invention, should have a molar ratio of Ca/P of not less than 0.2 and less than 0.6, and the total content of CaO plus $P_2O_5$ in the fiber glass should be not less than 80 wt%.

If the molar ratio of Ca/P is less than 0.2, the viscosity of the molten glass becomes so low as to make it difficult to form fibers therefrom. On the contrary, if the molar ratio of Ca/P is not less than 0.6, it becomes hard to melt the glass or the viscosity of the molten mass becomes too high to spin fibers therefrom. Even if fibers might be formed from a glass having a molar ratio of Ca/P of not less than 0.6, the fibers become opaque due to devitrification and too weak to be applied for practical use. If the total content of CaO plus $P_2O_5$ is less than 80 wt%, the compatibility with living body of the resultant fiber glass becomes so poor as to suppress growth of new bone tissue thereby to retard repair and recovery of bone structure.

When the zeta potential of the glass is determined through the streaming potential determination method by flowing distilled water through the test specimen (the powder-form glass mainly composed of calcium phosphate and contained in the test cell), the glass should have a negative zeta potential, preferably a zeta potential of from —0.05 to —20.0 mV, in order that the glass be excellent in compatibility with the living body to facilitate early growth of new bone tissue. A glass having a zeta potential ranging within —0.2 to —10.0 mV is particularly preferred to accerelate formation of new bone. In order to prepare a fiber glass having a negative zeta potential, it is essential to maintain the temperature of the molten mass of the starting material mixture at the step of forming fibers within the range of from 800° C. to 1400° C. and to control the content of inorganic oxides in the starting material mixture within the range of up to 20 wt%. A fiber glass having a zeta potential of from —0.05 to —20.0 mV can be formed by maintaining the temperature of the molten mass within the range of from 900° C. to 1300° C. and by controlling the content of inorganic oxides within the range of from 1 to 15 wt%. If the temperature of the molten mass is lower than 800° C. and the content of inorganic oxides exceeds 20 wt%, the resultant fiber glass has a positive zeta potential. On the other hand, if the temperature of the molten mass is higher than 1400° C. and no inorganic oxide is contained in the starting material mixture, the resultant fiber glass has a zeta potential of less than —20.0 mV.

Although the fiber glass of the invention may be used to fill a defect or hollow portion of bone in the as-prepared form of long filament or cotton-like staple, a woven fabric, such as cloth or gauze, may be formed from the filaments so that the woven fabric is used to fill or wound around the defect or hollow portion of bone. Repair or recovery of the defect of bone can be realized within a shorter period when the fiber glass of the invention used to fill the defect and a cloth or gauze made of the fiber glass is wound around the defect, when compared to the case where filling of the defect with the fiber glass is used alone. The fiber glass of long filament form, according to the invention, may be woven into a cloth or gauze by using a commercially available manual or automatic weaving machine.

It is preferred that the fibers mainly composed of calcium phosphate, according to their invention, have the surfaces coated with a calcium phosphate compound. The compatibility with living body of the fiber glass of the invention can be further improved to facilitate growth of new bone and to accerelate repair and recovery of the living bone structure integrally unified with the filled fiber glass, if the surface of each fiber mainly composed of calcium phosphate is coated with a calcium phosphate compound.

The surface of each glass fiber may be coated with or have deposited thereon a calcium phosphate compound by dipping the glass fibers mainly composed of calcium phosphate in a solution containing phosphoric ions, such as a solution of ammonium hydrogenphosphate or a mixed solution of phosphoric acid and ammonia, to allow the phosphoric ions existing in the solution to react with calcium ions in the glass fibers to form a calcium phosphate compound over the surface of each fiber. According to this process, the calcium phosphate compound deposited on the surface of each fiber has a molar ratio of Ca/P of from 0.8 to 1.7. Alternatively, a slurry of a calcium phosphate compound having a molar ratio of Ca/P of from 1.0 to 2.0 is prepared, and the glass fibers of the invention are dipped in the slurry to allow the calcium phosphate compound to adhere on the surface of each fiber followed by drying.

In the process of depositing a calcium phosphate compound on the surface of each fiber using a solution containing phosphoric ions, the solution may preferably have a pH value of 2 to 7. If the pH value of the solution is less than 2, the fiber glass mainly composed of calcium phosphate deteriorates so as to have a strength weaker than that required for practical use. On the contrary, if the pH value of the used solution is higher than 7, the amount of calcium phosphate compound depositing on the surface of each fiber becomes too small to reform and improve the surface.

A cloth or gauze may be woven from the reformed fibers of long filament form having the calcium phosphate compound on the surfaces thereof, or a cloth or gauze may be initially woven from fibers of long filament form and then the woven cloth or gauze is subjected to either of the aforementioned reformation treatments.

The fiber glass mainly composed of calcium phosphate, according to invention, may be used in the surgical or orthopedic operations and may also be used to fill in a defect formed at the vicinity of dental root canal due to pyorrhea alveolaris.

The present invention will be described more specifically by referring to some examples thereof.

EXAMPLES OF THE INVENTION

Example 1

Each of the starting material mixtures shown in the following Table 1 was prepared and melted in a pot provided with a nozzle at the bottom thereof to allow the molten mass to flow through the nozzle. The thus spun glass fibers were taken up around a drum to form filaments each having a diameter of 10 to 20 microns. The process conditions and the results are shown in Table 1.

TABLE 1

| Run No. | Molar Ratio of Ca/P | CaO + $P_2O_5$ (wt %) | Content of Inorganic Oxides Other Than Calcium Compound and Phosphorous Compound (wt %) | Starting Materials | Formation of Fiber | Devitrification | Melting Temperature (°C.) |
|---|---|---|---|---|---|---|---|
| 1 | 0.10 | 95 | 5 | CaO, $NH_4H_2PO_4$, $Al_2O_3$, $Na_2O$ | No. | — | 750 |
| 2 | 0.10 | 80 | 20 | Same as above | No. | — | 800 |
| 3 | 0.10 | 60 | 40 | Same as above | No. | — | 850 |
| 4 | 0.20 | 95 | 5 | $CaCO_3$, $H_3PO_4$, $Fe_2O_3$ | Yes | Not Observed | 950 |
| 5 | 0.20 | 80 | 20 | Same as above | Yes | Not Observed | 950 |
| 6 | 0.20 | 60 | 40 | Same as above | Yes | Not Observed | 1000 |
| 7 | 0.50 | 95 | 5 | $Ca(OH)_2$, $(NH_4)_2HPO_4$, MgO | Yes | Not Observed | 1050 |
| 8 | 0.50 | 80 | 20 | Same as above | Yes | Not Observed | 1080 |
| 9 | 0.50 | 60 | 40 | Same as above | Yes | Not Observed | 1100 |
| 10 | 0.59 | 95 | 5 | $Ca(OH)_2$, $(NH_4)_2HPO_4$, MgO | Yes | Not Observed | 1150 |
| 11 | 0.59 | 80 | 20 | Same as above | Yes | Not Observed | 1180 |
| 12 | 0.59 | 60 | 40 | Same as above | Yes | Not Observed | 1200 |
| 13 | 1.0 | 95 | 5 | $CaHPO_4$, $Al_2O_3$ | Yes | Observed | 1250 |
| 14 | 1.0 | 80 | 20 | Same as above | Yes | Observed | 1270 |
| 15 | 1.0 | 60 | 40 | Same as above | Yes | Observed | 1300 |

As should be apparent from the results in Table 1, the glasses each having a molar ratio of Ca/P of 0.10 could not form fibers, because the viscosities of the molten glasses were too low. On the other hand, although the glasses each having a molar ratio of Ca/P of 1.0 could be spun in the form of fiber, they were devitrified at the fiber forming step so as to be often broken so that continuous fibers could not be formed therefrom.

Fibers of long filament form could be produced, without serious breakdown of the spun fibers, in Run Nos. 4 to 12.

Each of the fibers produced in Run Nos. 1 to 15 was pulverized into a powder with which a test cell of a streaming potential determination device (Model ZP-10B, available from Shimazu Seisakusho, Ltd.) was filled, and distilled water was passed therethrough to determine the zeta potential of each glass. The results are shown in Table 2.

TABLE 2

| Run No. | 1 | 2 | 3 | 4 | 5 | 6 | 7 | 8 |
|---|---|---|---|---|---|---|---|---|
| Zeta Potential (mV) | −1.0 | −1.0 | −0.1 | −8.0 | −10.0 | −1.0 | −6.0 | −4.0 |
| Run No. | 9 | 10 | 11 | 12 | 13 | 14 | 15 | |
| Zeta Potential (mV) | −1.0 | −1.2 | −0.1 | −0.1 | −1.0 | −1.2 | −0.2 | |

Example 2

With each of the fiber glasses produced in Run Nos. 4 to 12 in Example 1 an artificially formed defect (3 mm$\phi$×4 mmL) in a femur of a rabbit was filled, and the portion filled with each glass fiber was inspected after the lapse of twelve weeks. The results revealed that the defects filled with fiber glasses of Run Nos. 4, 7, 8 and 10 were remedied with the fibers unified substantially integrally with the surrounding bone tissue. The volume of newly formed bone was slightly smaller than the cases where fiber glasses of Run Nos. 4, 7, 8 and 10 were used, when the defects were filled with either one of the fiber glasses produced by Run Nos. 5 and 11. Each of the defects filled with any one of the fiber glasses produced by Run Nos. 6, 9 and 12 was observed to reveal that new bone grew to cover only the portions of the filling fibers, the fibers being not unified integrally with the growing bone tissue.

Example 3

The same starting material mixtures as used in Run Nos. 4 and 8 in Example 1 were put into the same pot provided with a nozzle at the bottom thereof. The temperature of the content in the pot was maintained at 1000° C. for the Run No. 4 sample and maintained at 1120° C. for the Run No. 8 sample to allow the molten mass to flow through the nozzle. High pressure air was blown onto the discharged effluents to try to prepare cotton like staples each having a diameter ranging within 10 to 50 microns. The results were that cotton-like staples could be prepared from the starting material mixtures of Run Nos. 4 and 8.

The thus prepared staples were filled in defects (3 mm$\phi$×4 mmL) artificially formed in femurs of rabbits, and the post-operation recovery of the defects was observed, to reveal that a large quantity of new bone was formed over the surfaces of filling staples after the lapse of four weeks in both cases.

Example 4

The fiber glasses produced by Run Nos. 4 and 8 in Example 1 were dipped in aqueous ammonia solutions to which phosphoric acid had been added and having a pH value of 1.0, 2.0, 4.0, 6.0, 7.0 and 8.0, respectively, for 30 minutes to treat the surfaces of the fibers. The fibers treated at pH 1.0 were adversely attacked by the treating solution so as to have rugged surfaces. The fibers treated at pH 8.0 had the surfaces which were scarcely covered with the deposition. The surfaces of the fibers treated at pH 2.0 to 7.0, respectively, were covered by the deposition, and particularly the surfaces of the fibers treated at pH 4.0 and 6.0 were covered with the deposition uniformly.

The deposition over the surfaces of the fibers was observed through an electron microscope to analyze the same, whereby it was revealed that the deposited compound is a calcium phosphate compound having a molar ratio of Ca/P of about 1.

With each of the two fiber glasses (Run Nos. 4 and 8) treated at pH 4.0 a defect in the femur of a rabbit was filled, similarly to Example 3, and the growth of new bone was observed after three weeks. The growth of new bone over the surfaces of filling fibers was substantially equivalent to that observed in Example 3.

Example 5

The fiber glass produced by Run No. 8 in Example 1 was woven into a cloth (Width: 5 cm, Length: 5 cm) using a weaving machine. An additional cloth was prepared from the same fiber glass followed by dipping the same in an aqueous ammonium phosphate solution having a pH value of 4.0, the solution being the same as used in Example 4, to deposit a calcium phosphate compound (Molar Ratio of Ca/P=about 1.2) over the surfaces of the filaments. Separately, the filament of Run No. 8 fiber glass was treated at pH 4.0, similarly to Example 4, and a cloth was woven from the treated filament.

With each of the thus prepared cloths a defect artificially formed in a femur of a rabbit was filled, similarly to Example 4, and the thus filled defect was further covered by the cloth followed by suturing. Inspection conducted three weeks after the operation revealed that a large quantity of new bone had grown in the defect filled and covered with either one of the cloths, the volume of new bone being appreciably larger than those observed in Example 4. Particularly, the defects filled and covered with the cloths having the surfaces deposited with the calcium phosphate compound were remedied by appreciably larger volume of growing new bone.

Example 6

In accordance with a similar procedure as in Example 1, hydroxyapatite and $H_3PO_4$ were mixed to prepare a glass powder having a molar ratio of Ca/P of 0.5 and the total content of CaO plus $P_2O_5$ of approximately 100%. The glass powder was melted at 1000° C. and fiber glass was formed from the molten glass. The zeta potential of the formed fiber glass was determined similarly to Example 1 to find that the zeta potential was −20.0 mV.

With the thus produced fiber glass a defect (3 mm$\phi$×4 mmL) artificially formed in a femur of a rabbit was filled, and the post-operation course of the rabbit was observed. The observation showed that a large volume of new bone had grown over the surfaces of the filling fibers.

Comparative Example 1

Using CaO, $H_3PO_4$ and $Al_2O_3$ as the starting materials, a fiber glass having a molar ratio of Ca/P of 0.30 and a total content of CaO plus $P_2O_5$ of 80 wt%, the content of $Al_2O_3$ being 20 wt%, was produced from a molten mass maintained at 780° C. The glass fiber was pulverized into a fine powder which was subjected to zeta potential determination to find that the zeta potential thereof was +0.1 mV.

With the aforementioned fiber glass a defect formed in a femur of a rabbit was filled, and the post-operation condition after the lapse of three weeks was observed. The result was that the surfaces of the filled fibers were scarcely covered by new bone although a small volume of new bone had grown from the living bone tissue surrounding the defect.

Comparative Example 2

Using $CaCO_3$, $NH_4H_2PO_4$ and $Al_2O_3$ as the starting materials, a fiber glass having a molar ratio of Ca/P of 1.7 and a total content of CaO plus $P_2O_5$ of 50 wt%, the content of $Al_2O_3$ being 50 wt%, was produced from a molten mass maintained at 1550° C. The zeta potential of the fiber glass was determined, similarly to Example 1, to find that the zeta potential thereof was +0.30 mV.

With the fiber glass a defect formed in a femur of a rabbit was filled, and the post-operation condition after the lapse of three weeks was observed. The result was substantially similar to that observed in Comparative Example 1.

In the foregoing description, the present invention has been specifically disclosed by referring to some examples thereof. However, it should be appreciated that various modifications and variations can be easily made by those skilled in the art without departing from the spirit of the invention. It is, thus, intended to include all such modifications and variations within the wide scope of the present invention defined by the appended claims.

What is claimed is:

1. A fiber glass for filling in a defect or hollow portion of bone, said fiber glass having a negative zeta potential and containing calcium phosphate having a molar ratio of Ca to P of not less than 0.2 and less than 0.6, and the total content of CaO plus $P_2O_5$ in the fiber glass, based on the weight of the fiber glass, being not less than 80% by weight, the surface of the fiber glass being coated with a calcium phosphate compound.

2. The fiber glass according to claim 1 wherein said calcium phosphate compound of the coating is selected from the group consisting of tetracalcium phosphate, hydroxyapatite, tricalcium phosphate, animal bones and mixtures thereof.

3. The fiber glass according to claim 1, wherein said fiber glass has a zeta potential of $-0.05$ to $-20.0$ mV.

4. The fiber glass according to claim 1, wherein said fiber glass has a zeta potential of $-0.2$ to $-10.0$ mV.

5. The fiber glass according to claim 1, wherein said fiber glass is prepared by cooling a molten mass containing a mixture of at least one phosphorous-containing compound with at least one compound selected from the group consisting of calcium phosphate compounds and other calcium-containing compounds.

6. The fiber glass according to claim 5, wherein said molten mass contains an inorganic oxide.

7. The fiber glass according to claim 6, wherein said inorganic oxide is selected from the group consisting of alumina, silica, sodium oxide, iron oxide, magnesium oxide, kaolin and mixtures thereof.

8. The fiber glass according to claim 5, wherein said calcium phosphate compound contained in said molten mass is selected from the group consisting of tetracalcium phosphate, hydroxyapatite, tricalcium phosphate, animal bones and mixtures thereof.

9. The fiber glass according to claim 5, wherein said other calcium-containing compound is selected from the group consisting of quick lime, slaked lime, calcium carbonate and mixtures thereof.

10. The fiber glass according to claim 5, wherein said phosphorous-containing compound is selected from the group consistng of triammonium phosphate, ammonium hydrogenphosphate, sodium phosphate, phosphoric acid and mixtures thereof.

11. The fiber glass according to claim 5, wherein said molten mass has a melting temperature of 800° C. to 1400° C. and wherein said glass contains 0 to 20%, by weight, of an inorganic oxide.

12. The fiber glass according to claim 5, wherein said molten mass has a melting temperature of 900° C. to 1300° C. and wherein said glass contains 1 to 15%, by weight, of an inorganic oxide.

13. The fiber glass according to claim 1, wherein the coating is formed by dipping the fiber glass in a solution containing phosphoric ions and having a pH value of from 2 to 7 to deposit said calcium phosphate compound on the surface thereof, and wherein the molar ratio of Ca to P of the deposited calcium phosphate compound ranges within 0.8 to 1.7.

14. The fiber glass according to claim 1, wherein the calcium phosphate compound of the coating has a molar ratio of Ca to P of 1.0 to 2.0 and is then subjected to drying.

15. The fiber glass according to claim 1, wherein said fiber glass is of filament form or staple fiber form.

16. The fiber glass according to claim 13, wherein said solution containing phosphoric ions is selected from the group consisting of a solution of ammonium hydrogenphosphate and a mixed solution of phosphoric acid and ammonia.

* * * * *